United States Patent [19]

Gregory

[11] Patent Number: 4,759,358
[45] Date of Patent: Jul. 26, 1988

[54] GAS ADMINISTRATION APPARATUS

[75] Inventor: Raymond S. Gregory, Bingley, England

[73] Assignee: The BOC Group, Inc., Montvale, N.J.

[21] Appl. No.: 75,369

[22] Filed: Jul. 20, 1987

[30] Foreign Application Priority Data

Aug. 8, 1986 [GB] United Kingdom ............... 8619419

[51] Int. Cl.$^4$ ............................................ A61M 16/00
[52] U.S. Cl. ........................... 128/200.14; 128/200.19; 137/637.1
[58] Field of Search .................... 128/200.14, 200.19; 137/637.1; 74/483 K

[56] References Cited

U.S. PATENT DOCUMENTS

| | | | |
|---|---|---|---|
| 4,307,718 | 12/1981 | Schreiber | 137/637.1 X |
| 4,308,865 | 1/1982 | Hay | 128/200.19 X |
| 4,346,701 | 8/1982 | Richards | 137/637.1 |
| 4,351,327 | 9/1982 | Rinne et al. | 137/637.1 X |
| 4,434,790 | 3/1984 | Olesen | 137/637.1 X |
| 4,463,754 | 8/1984 | McDonald | 137/637.1 X |
| 4,493,318 | 1/1985 | Mohr et al. | 137/637.1 X |

Primary Examiner—Gerald A. Michalsky
Attorney, Agent, or Firm—Roger M. Rathbun; Larry R. Cassett

[57] ABSTRACT

An interlock system for use with two or more vaporizers when mounted in plug-in fashion on the back bar of an anaesthesia machine includes a spacer 22 of generally channel shaped section having spaced arms 10, 11 engageable by pins which extend outwardly from individual vaporizers when a concentration dial on the vaporizer is moved from an off position to an operative position. Outward movement of the pins causes the spacer to slide on the back bar between adjacent units thereby preventing outward movement of a pin on a similar adjacent unit.

5 Claims, 1 Drawing Sheet

GAS ADMINISTRATION APPARATUS

FIELD OF THE INVENTION

The present invention relates to gas flow units adapted to mounted on gas administration apparatus in a removable plug-in fashion and in particular to gas flow units such as vaporisers which are adapted to be mounted on apparatus for the administration of gaseous anaesthetics, analgesics or other medical gases or gas mixtures such as oxygen or air (which for convenience will hereinafter be referred to collectively as anaesthetics).

BACKGROUND OF THE INVENTION

In United Kingdom patent specification No. 1 385 670, there is described a gas administration apparatus on which one or more gas flow units can be mounted in a removable plug-in fashion. This known plug-in system has proved to be very popular in that it simplifies the installation and removal of gas flow units from the apparatus thereby facilitating maintenance and cleaning of the units as well as the replacement of a unit should it fail during an operation.

It is common practice for an anaesthesia apparatus to have mounted on it two or more separate vaporisers for delivering different volatile anaesthetics so that the same basic anaesthesia apparatus can be used during a series of surgical operations to meet the needs of different patients. In UK patent No 2 052 271, there is described an interlocking system which prevents two different anaesthetics being delivered to a patient at the same time or otherwise becoming mixed. This known interlocking system includes pins associated with each vaporiser which, when its concentration dial is moved from the off position, causes the pins to extend outwardly and block the movement of corresponding pins on immediately adjacent vaporisers thereby preventing the concentration dials of these other vaporisers from being operated. With this arrangement it is impossible to switch more than one vaporiser into a gas circuit at any one time.

This known interlocking system works well when there are two or more units arranged side-by-side. However, if the middle unit of, for example, three units is removed for any reason then the interlocking action of the first unit cannot be transmitted to the third unit and vice versa. This problem has been overcome by using non-functional (dummy) second units or merely applying warning labels to indicate that no interlocking system is available.

OBJECT OF THE INVENTION

It is an aim of the present invention to provide an interlocking system for a combination of two or more gas flow unit when mounted on a gas administration apparatus in releasable plug-in fashion, which ensures that only a selected one of the two or more alternative units can be connected to a gas circuit at any one time.

SUMMARY OF THE INVENTION

The present invention comprises in combination at least two gas flow units each mounted on a gas administration apparatus in a removable plug-in fashion, each unit including means which when moved from an off to an operative position admits to the unit a gas from a supply provided by the apparatus and an interlocking system including at least one pin associated with each unit which, when said means is moved towards its operative position, extends outwardly from the unit to engage and move a spacer mounted for sliding movement on the apparatus between adjacent units towards a similar adjacent unit thereby to prevent said means of the similar adjacent unit being moved towards its operative position.

BRIEF DESCRIPTION OF DRAWING

An embodiment of the invention will now be described, by way of example, reference being made to the Figures of the accompanying diagrammatic drawings in which.

DESCRIPTION OF PREFERRED EMBODIMENT

Figure 1:
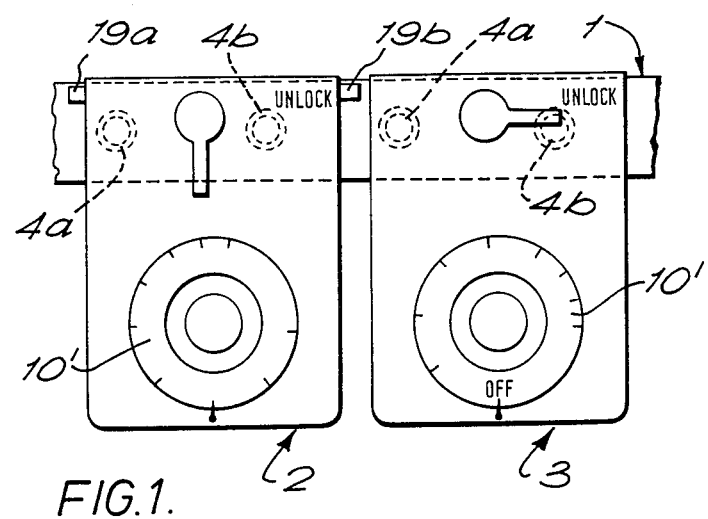
FIG. 1 is a schematic plan view of two alternative gas flow units (vaporisers) mounted on the back bar of an anaesthesia machine.

As shown in FIG. 1, the back bar 1 of an anaesthesia machine supports in a removable plug-in fashion two gas flow units in the form of vaporisers 2, 3 adapted to deliver different volatile anaesthetic agents. The vaporisers 2, 3 are mounted side-by-side on the back bar 1 and located by respective pairs of ports 4a, 4b upstanding from the back bar. Mounted on the top of each vaporiser 2, 3 is a concentration dial 10 controlling the admission to the vaporiser of a carrier gas. As is explained in UK patent No. 2 052 271 any rotational movement of a concentration dial 10 from its off position is transmitted via cams, cranks, spring loaded platforms and pins to two pins 19a, 19b which are caused to extend outwardly from the body of the vaporiser as shown with reference to vaporiser 2.

It is apparent that, whenever the concentration dial of a vaporiser is rotated into a position which provides for the admission of a carrier gas to the vaporiser, the two pins 19a, 19b will extend one to each side of the vaporiser. Then, when the dial 10 of vaporiser 2 has been moved away from the off position to its operating position to open an associated control valve then accordingly its pins 19a, 19b are extended which will prevent any operation of the concentration dial 10 on the vaporiser 3. Thus it is impossible to switch more than one of the vaporisers into the gas circuit at any one time.

As explained previously, this interlocking system works well when there are two vaporisers side-by-side as illustrated in FIG. 1 or if there are two or more vaporisers located side-by-side. However, it will be apparent that should there be for example three vaporisers mounted side-by-side and then the middle vaporiser is removed then there would be nothing to prevent each of the remaining two vaporisers from being operated since the respective pins 19a, 19b would not make contact with each other.

Figure 2:
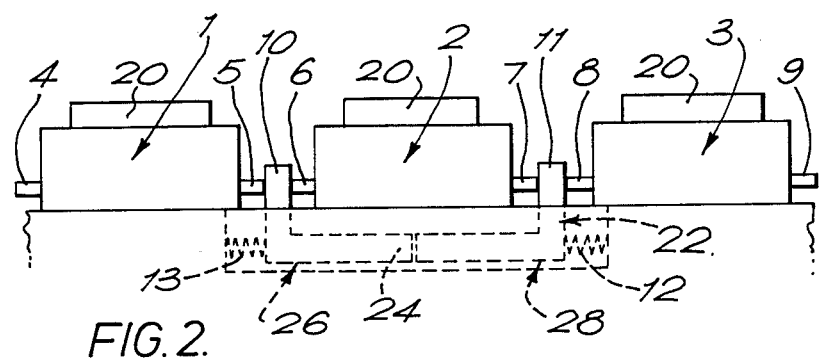
FIG. 2 is a schematic rear view of three alternative gas flow units (vaporisers) mounted on the back bar of an anaesthesia machine.

Referring now to FIG. 2, there is shown three vaporisers 1, 2 and 3 mounted on a back bar in a releasable plug-in fashion as described with reference to FIG. 1. For convenience, the ports 4a, 4b have not been illustrated. Each vaporiser 1, 2, 3 has a concentration dial 20 which when moved from its off position causes pins 4, 5; 6, 7; and 8, 9 to extend outwardly from the vaporiser. A spacer 22 is mounted for sliding movement on the back bar. The spacer is generally channel-shaped with two spaced arms 10, 11 extending from a web part 24.

As shown, the arm 10 extends between the vaporisers 1 and 2 and the arm 11 extends between the vaporisers 2 and 3. The spacer 22 is divided along the web 24 to form two individual parts 26, 28 each capable of moving towards and away from the other part. The parts are biased centrally relative to the vaporiser 2 by light springs 12, 13.

In use, if the concentration dial 20 of vaporiser 1 is moved from its off position both pins 4, 5 will move outwardly. This will cause pin 5 to engage and move arm 10 to the right (as shown) which will block outward movement of pin 6 on vaporiser 2 and thus prevent the admission of gas to the vaporiser 2. Further, rightward movement of part 26 will be transmitted to part 28 of the spacer 22 which will also move to the right thereby causing arm 11 to block outward movement of pin 8 on vaporiser 3 and thus prevent the admission of gas to the vaporiser 3.

If the concentration dial 20 of vaporiser 2 is moved from its off position pins 6, 7 will move outwardly to engage and move respectively arm 10 to the left (as shown) and arm 11 to the right (as shown). Arm 10 will block outward movement of pin 5 on the vaporiser 1 and thus prevent the admission of gas to the vaporiser 1 and arm 11 will block outward movement of the pin 8 on vaporiser 3 and thus prevent the admission of gas to the vaporiser 3.

Should vaporiser 2 be removed for any reason the interlocking movement will still be transmitted between the vaporisers 1 and 3 since the movement of for example, rod 5 will be transmitted directly by parts 26, 28 so that arm 11 blocks outward movement of the pin 8 and vice versa.

It will be appreciated that with the system described above there is no danger of two or more anaesthetic vaporisers being switched into the gas circuit at the same time. It will be appreciated that the system is not restricted to a gang of three vaporisers but could be used with three or more gas flow units.

I claim:

1. In combination, at least two gas flow units each mounted on a gas administration apparatus in a removable plug-in fashion, each unit including means which when moved from an off to an operative position admits to the unit a gas from a supply provided by the apparatus and an interlocking system including at least one pin associated with each unit which, when said means is moved towards its operative position, extends outwardly from the unit to engage and move a spacer mounted for sliding movement on the apparatus between adjacent units towards a similar adjacent unit thereby to prevent said means of the similar adjacent unit being moved towards its operative position.

2. A combination as claimed in claim 1, in which the spacer is generally channel-shapped having spaced arms engageable by pins, which arms extend from a web part.

3. A combination as claimed in claim 2, in which the distance between opposite faces of the arms is such that the arms will extend on each side of a unit when positioned between the arms.

4. A combination as claimed in claim 2 or 3, in which the spacer is divided along the web to form two individual parts each movable relative to the other part.

5. A combination as claimed in claim 4, in which means is provided for biasing the individual parts together so that opposed faces of the web engage each other.

* * * * *